United States Patent
Succar et al.

(10) Patent No.: US 10,857,060 B2
(45) Date of Patent: Dec. 8, 2020

(54) METHOD AND DEVICE FOR IMPROVING FUNCTIONAL STEREOPSIS IN INDIVIDUALS WITH CENTRAL VISION LOSS

(71) Applicant: Envision, Inc., Wichita, KS (US)

(72) Inventors: Tony Succar, Los Angeles, CA (US); Saeideh Ghahghaeinezamabadi, Berkeley, CA (US); Laura Lynn Walker, Orinda, CA (US)

(73) Assignee: Envision, Inc., Witchita, KS (US)

( * ) Notice: Subject to any disclaimer, the term of this patent is extended or adjusted under 35 U.S.C. 154(b) by 96 days.

(21) Appl. No.: 15/964,111

(22) Filed: Apr. 27, 2018

(65) Prior Publication Data

US 2018/0311103 A1 Nov. 1, 2018

Related U.S. Application Data

(60) Provisional application No. 62/491,602, filed on Apr. 28, 2017.

(51) Int. Cl.
*A61B 3/00* (2006.01)
*A61B 3/10* (2006.01)
*A61H 5/00* (2006.01)
*A61B 3/08* (2006.01)

(52) U.S. Cl.
CPC ........... *A61H 5/005* (2013.01); *A61B 3/08* (2013.01)

(58) Field of Classification Search
CPC .. A61B 3/08; A61B 3/032; A61B 3/02; A61B 3/024
USPC ............. 351/200, 203, 205–206, 209–211, 351/221–223, 243–246
See application file for complete search history.

(56) References Cited

U.S. PATENT DOCUMENTS

| | | | |
|---|---|---|---|
| 8,057,036 B2 | 11/2011 | Hess et al. | |
| 8,066,372 B2 | 11/2011 | Cooperstock et al. | |
| 2012/0069296 A1* | 3/2012 | Li | A61B 3/08 351/201 |
| 2013/0044290 A1* | 2/2013 | Kawamura | A61B 3/032 351/201 |

OTHER PUBLICATIONS

Walker et al., Envision Research Institute, "Retaining Depth Perception in Age-Related Macular Degeneration", 2017, 23 pages.

\* cited by examiner

*Primary Examiner* — Brandi N Thomas
(74) *Attorney, Agent, or Firm* — Paterson Thuente Pedersen, P.A.

(57) ABSTRACT

A method of improving stereopsis and devices for improving stereopsis in a patient, including facilitating development of a new stereo preferred retinal locus by presenting the patient with dichoptic images that require simultaneous use of both eyes to accomplish a visual task.

6 Claims, 4 Drawing Sheets

METHOD AND DEVICE FOR IMPROVING FUNCTIONAL STEREOPSIS IN INDIVIDUALS WITH CENTRAL VISION LOSS

CROSS-REFERENCE TO RELATED APPLICATION

The present application claims the benefit of U.S. Provisional Application No. 62/491,602, filed Apr. 28, 2017 entitled "Method and Device for Improving Functional Stereopsis in Individuals with Central Vision Loss," which is hereby incorporated herein in its entirety by reference.

TECHNICAL FIELD

Embodiments of the invention generally relate to human vision, stereopsis and macular degeneration or other central vision impairing eye diseases. More particularly the invention relates to treating and improving stereo perception in patients who have suffered central vision loss, often to a greater degree in one eye than in the other.

BACKGROUND

Stereopsis, also referred to as stereoscopic vision or stereo vision, is the primary way that human beings judge depth within approximately arm's length. Stereopsis occurs because of the slight mismatch in the image received in the right eye as compared to the left eye because of the separation of the eyes and their overlapping visual fields. Under normal circumstances stereopsis occurs so long as there is a single binocular vision and the brain is able to process the two images of from the two eyes to provide a single perception of the world that includes a judgment of depth. Stereopsis provides the perception of depth in, for example, three-dimensional movies, Viewmasters and various virtual reality imaging systems. To obtain stereoscopic vision an individual must be capable of receiving a fairly well focused and perceived image of their surroundings in each eye.

Loss of binocular visual function in stereopsis can occur in numerous visual disorders. A variety of eye diseases can selectively damage central vision while leaving more peripheral vision intact. For example, macular degeneration whether age-related macular degeneration or another form of inherited macular degeneration, selectively damages the macula lutea of the retina. The macula is the area of the retina responsible for accurate central vision. At the center of the macula is located the fovea centralis which in a healthy eye corresponds to the "aiming point" in the visual field at which individuals direct their eyes for most accurate clear central vision. Accordingly, damage to the macula can leave the macular degeneration sufferer with a central scotoma. That is, a centrally located blind spot that, depending upon its size, can reduce central visual acuity in one eye mildly or dramatically. Another condition that can lead to a central blind spot is development of a macular hole.

In these circumstances, central vision in one eye is often impaired to a greater degree than in the other eye. This can lead to a partial or complete loss of stereoscopic vision with an attendant loss of depth perception that can cause significant impairment for many daily activities. Loss of stereopsis can interfere with driving, reading and picking up objects for example.

Stereopsis-based depth perception is an important component for many visually guided tasks. As discussed above, age-related macular degeneration can result in the development of bilateral central scotoma which can impair binocular function and stereopsis. Patients with poor stereopsis have been demonstrated to have difficulty with eye hand coordination and grasping objects for example. At least anecdotal reports suggest that reduced stereopsis may also have an impact on overall visual function as well as quality of life.

Previous research suggests that the preferred retinal locus (PRL) of the dominant eye or the eye with better vision often leads the fellow eye under binocular viewing conditions. However, this monocular PRL may fall within a scotoma of the fellow eye, which is the eye with greater vision loss, rendering the patient monocular at the point of fixation. Because the patient is monocular at the point of fixation stereo acuity is diminished. Diminished stereo acuity then leads to difficulty in performing tasks requiring stereo acuity.

Accordingly, patients who suffer central vision loss due to eye disease or injury would benefit greatly if they were able to, at least partially, recover stereo acuity.

SUMMARY

Embodiments of the invention can assist with the recovery of at least some stereopsis and improve stereo acuity for low vision patients with central vision loss. Example embodiments of the invention include methods and devices to assist in the recovery of stereoscopic vision by encouraging the development of a binocular preferred retinal locus (PRL) at a location in each eye where binocular vision is still possible. Example embodiments of the invention include the dichoptic display of a videogame which is played by a user and which is used to encourage the user who has central vision loss in at least one eye to use functional retina in the two eyes simultaneously.

Example embodiments of the invention include a dichoptic training intervention device and method for relocating a stereo or binocular preferred retinal locus (PRL) to fall on corresponding functional retinal points for improving depth perception. Individuals who suffer macular disease often experience a loss of their straight ahead vision because, as discussed above, the macula is the portion of the retina responsible for clear detailed straight ahead vision. The preferred retinal locus allows an individual with damaged macular function to utilize a different portion of the retina other than the fovea or macula as their point of fixation. While the PRL will demonstrate lesser visual acuity than fovea centered macular vision due to differences in retinal structure, improve stereopsis can still be attained.

Embodiments of the invention include dichoptic display of a videogame. Selected visual elements of the game are presented into each eye independently while some other visual elements of the game are presented to both eyes. To play the game successfully, a user must take advantage of functional retina in each of the two eyes simultaneously. Elements of the videogame that are seen only by one eye can be separated by the use of an anaglyph (red/green) display and glasses, by a polarized presentation or by use, for example on a tablet with stereo glasses or in a head mounted display adapted for virtual-reality presentation. For example Google Cardboard or Samsung VR may be utilized. A variety of techniques for providing separate images to each eye for a stereoscopic presentation are known to those skilled in the art. Any techniques that currently exist or are yet to be developed can be utilized in the context of the inventions disclosed herein.

In an example, over the course of five two-hour training sessions, eight individuals with central visual field loss due to age related macular degeneration demonstrated significant improvement in stereo vision as measured with Titmus stereo acuity placards. Eight research participants who played the game without dichoptic display did not experience a similar benefit. Two individuals from the control group were then crossed over to the experimental group. Both anecdotally reported improvements in activities of daily living including such activities as driving, reading and picking up objects. It is expected, though not presently confirmed, that improvements in stereopsis will correlate with improvements in activities of daily living as measured by application of an activity inventory.

According to the example, two participant groups were created. An experimental group performed dichoptic training with anaglyph glasses while a control group performed sham training with non-anaglyph glasses. With the non-anaglyph glasses all of the presented structures of the video game were visible to both eyes of the test subjects. Accordingly, the control group was not required or encouraged to utilize both eyes simultaneously to successfully accomplish the tasks of the experimental videogame.

Several factors were tested prior to and following the training sessions. First, stereo acuity utilizing the Titmus test was performed before each training session. Second, an activity inventory was utilized. The activity inventory includes an adaptive visual function questionnaire used to measure functional visual abilities. Third, scanning laser ophthalmoscopy (SLO) monocular fixation locus, microperimetry and optical coherence tomography (OCT) were performed. Fourth, a California central visual field test was performed. Finally, contrast sensitivity testing was done.

In the dichoptic training videogame according to an example embodiment of the invention, the videogame screen was structured so that when anaglyph glasses were worn structures that were under control of the computer program were presented in green and thus seen by one eye. A structure under control of the patient/player were presented in red and thus seen by the fellow eye. Background structures that act as a fusion lock were presented in yellow and thus, were visible to both eyes.

According to the experimental protocol, color calibration was performed prior to game play to ascertain that the various color images were being seen accurately by the right eye, by the left eye and by both eyes together. This included adjusting the screen colors for the right eye viewed objects and the left eye viewed objects to confirm that objects were seen by the appropriate eye and that objects to be seen by both eyes were, in fact, seen by both eyes.

A specific example embodiment is based on the classic arcade game Space Invaders. The aliens were presented in green while the spaceship or shooting station was presented in red. Thus, the aliens were visible only to the eye having the green visual filter while the spaceship or shooting station was visible to the eye having the red visual filter. Buildings of a cityscape acting as a fusion lock were presented in yellow and thus seen by both eyes through both the red and green visual filters.

Data disclosed herein suggests that approximately two thirds of low vision patients suffer from stereo blindness or loss of stereo acuity as a consequence of their condition.

The inventors have not identified any published data on the prevalence of stereo blindness in low vision patients. The inventors have gathered data on 30 patients having a median age of 80.5 years and a range of ages from 19 to 97 years. 70% of these patients with all diagnoses demonstrated stereo acuity of worse than 3000 arc minutes. 63% of these patients had no measurable stereo acuity based on the Titmus placard. Of all the patients in the group 60% had age related macular degeneration (N=18). The majority of patients with Aging Related Macular Degeneration (AMD or ARMD) demonstrated reduced stereo vision.

The proportion of low vision patients with AMD was 60% (N=18) the proportion of patients with AMD who were stereo blind was 83% (N=15).

Further information on the patients who participated in the dichoptic video game training is presented below:

|  | Median Age (Range) | Gender F:M | Better Eye (RANGE) | Worse Eye (RANGE) |
| --- | --- | --- | --- | --- |
| Control (n = 8) | 81 (47-97) | 6:2 | 20/86 (20/70-20/192) | 20/160 (20/121-20/200) |
| Experimental (N = 8) | 73 (61-83) | 7:1 | 20/86 (20/40-20/147) | 20/127 (20/46-20/160) |

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figures 1, 2:
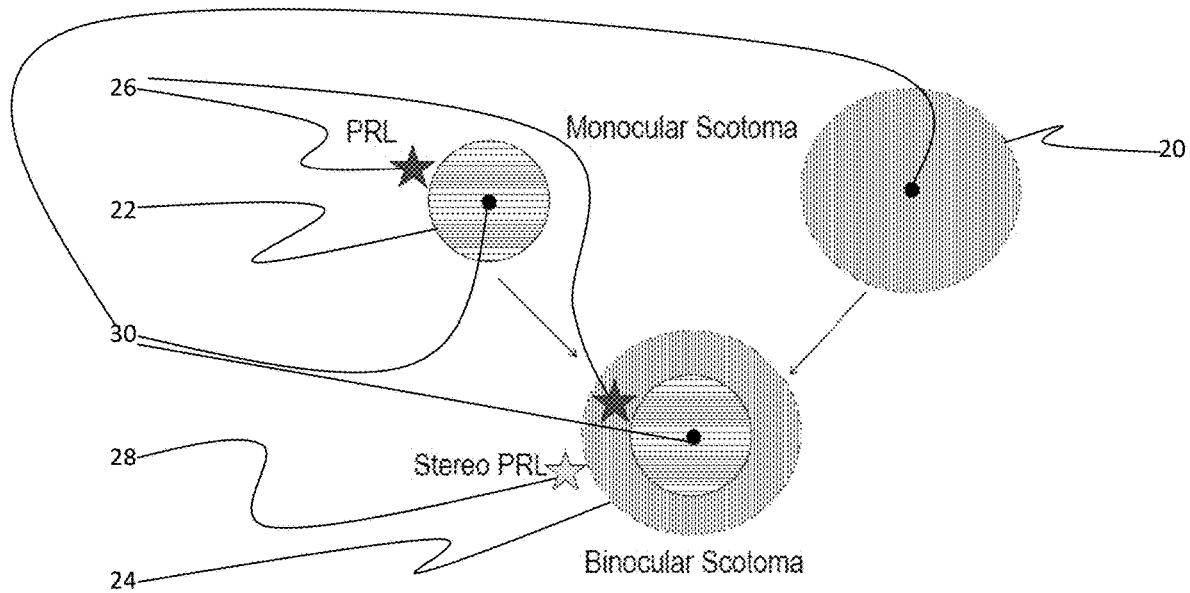
FIG. 1 is a depiction of two unequal sized monocular scotomas including a preferred retinal locus and a stereo preferred retinal locus.
FIG. 2 is a chart defining experimental participant groups.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Referring to FIGS. 1-6, example embodiments of the invention include a method and device for improving stereopsis in patients who have suffered central visual field loss due to a variety of conditions including, but not limited to, age related macular degeneration (ARMD or AMD). Stereopsis is improved by encouraging the patient to establish a new binocular PRL at corresponding retinal points in each eye where functional vision exists in each eye.

It has been observed that approximately two thirds of low vision patients suffer from stereo blindness and loss of binocularity as a consequence of their disease or injury. So, while embodiments of the invention are discussed herein largely in the context of age related macular degeneration and other forms of macular degeneration, this should not be considered limiting as the methods and devices discussed herein are expected to provide benefit to low vision patients who have suffered central vision loss from various causes.

Referring particularly to FIG. 1, depicted are a right monocular scotoma 20, left monocular scotoma 22, a resulting binocular scotoma 24, monocular preferred retinal locus (PRL) 26 and stereo PRL 28. A location in the visual field corresponding to fovea 30 is indicated by a black dot in each representation. In many eye diseases causing central scotoma it is typical for right monocular scotoma 20 to be a different size, shape or size and shape from left monocular scotoma 22. It is common for central scotoma in one or both eyes to be irregular in shape. The depiction of circular right monocular scotoma 20 and circular left monocular scotoma 22 according to the drawings herein is merely for simplicity and should not be considered limiting. In the depicted example, right monocular scotoma 20 is substantially larger than left monocular scotoma 22. This results in a combined binocular scotoma 24 whose overall extent corresponds in size to the larger of the two scotomas but which may include an area of complete binocular vision loss and an area of partial binocular vision loss. In the depicted example, in areas where right monocular scotoma 20 extends beyond left monocular scotoma 22 monocular vision exists even with both eyes open. When fovea 30 is located within a scotoma the human visual system may establish another location on the retina to utilize as an "aiming point" or substitute for the fovea. This is referred to as the preferred retinal locus and is generally located just outside the scotomatous area. As can be seen in FIG. 1, a monocular preferred retinal locus 26 and a binocular preferred retinal locus 28 will often be located in different non-corresponding locations in view of the different size of the right monocular scotoma 20 and left monocular scotoma 22.

Figure 7:
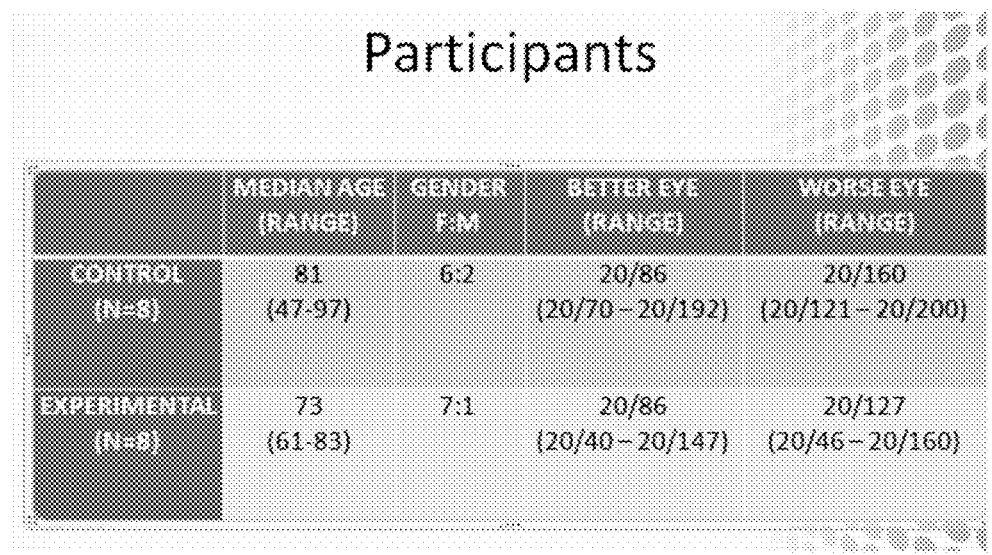
FIG. 7 is a chart defining experimental participant groups.

Referring to FIG. 2 and FIG. 7, example embodiments of the invention were tested with two participant groups including an experimental group and a control group. Members of the experimental group performed dichoptic training with anaglyph glasses. Anaglyph glasses are used here as an example of one way to present dichoptic images to individuals to be treated or tested. Dichoptic images may also be presented by use of polarized glasses, a telebinocular, or a variety of other known methods to provide a first image to a right eye and a second image to the left eye. It is intended that the invention cover all methods of presenting a dichoptic image whether currently known or to be established in the future.

Figure 3:
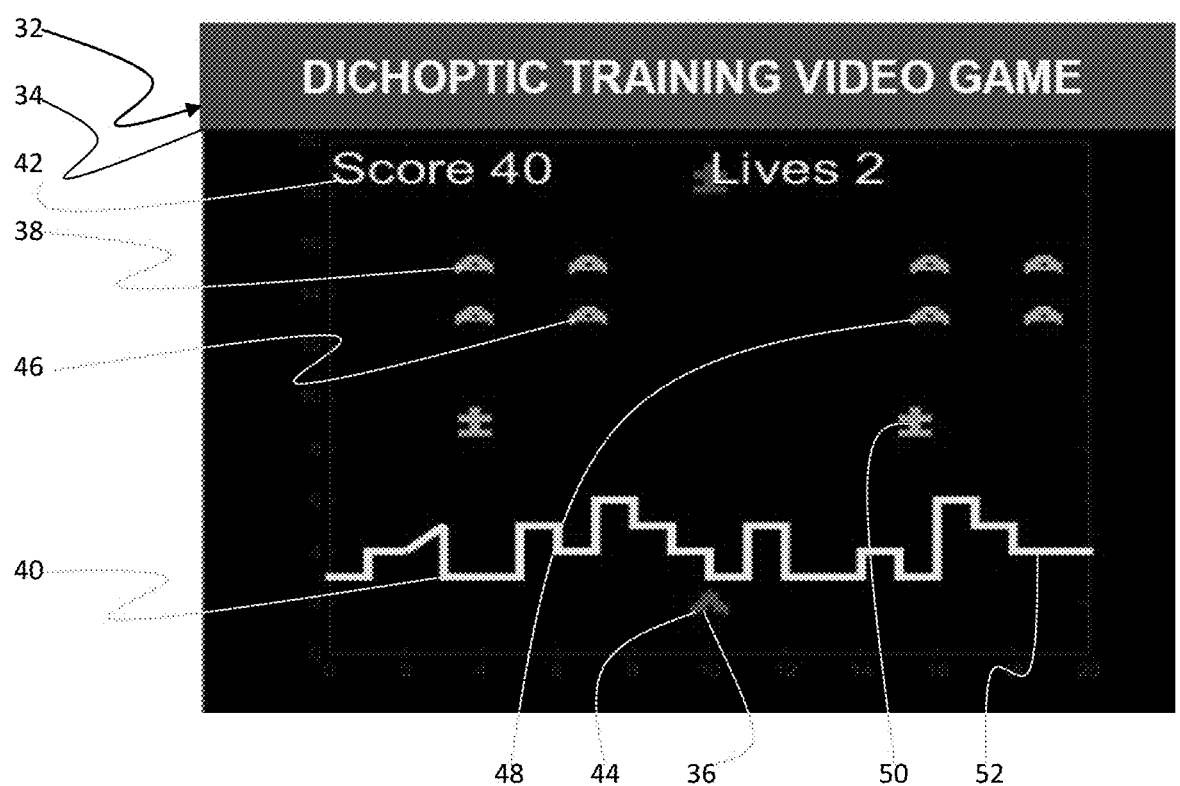
FIG. 3 is a screenshot of a dichoptic training videogame as utilized according to example embodiments of the invention.

Referring to FIG. 3, screenshot 32 of dichoptic training videogame 34, according to an example embodiment of the invention, is depicted. Screenshot 32 is loosely based on the classic videogame Space Invaders. A public domain generic version of the game was utilized as a basis for the modified game version disclosed herein. The modified game version is altered to present dichoptic images to the player so that the game cannot be successfully played without utilization of at least some degree of binocular vision.

Screenshot 32 generally presents right eye image 36, left eye image 38, binocular fusion lock 40 and scoreboard 42.

Right eye image 36, in this example embodiment, includes shooting station 44. Shooting station 44 is seen by the right eye and is controlled in a known fashion to move along a lower portion of screenshot 32.

Left eye image 38, in this example embodiment, includes attacking aliens 46. Attacking aliens 46 gradually move from the top of the screen to the bottom of screenshot 32 or across the width of screenshot 32. Attacking aliens 46 include vertical moving aliens 48 and horizontal moving aliens 50. Both vertical moving aliens 48 and horizontal moving aliens 50 are seen by the left eye and are controlled by the computer program. As is known in the prior art, attacking aliens 46 disappear when struck by shots from shooting station 44.

Binocular fusion lock 40 presented in this example embodiment, includes city skyline 52. City skyline 52 is stationary within screenshot 32 and is structured to be seen by both eyes simultaneously. Accordingly, city skyline 52 acts as binocular fusion lock 40 and assists in the patient maintaining binocularity during game play. Binocular fusion lock 40 is generally more effective if it is large and extends a substantial portion of the width and/or height of the screen. Conversely, right eye image 36 and left eye image 38 are expected to be more effective if they are relatively small and take up a small portion of the screen thus providing targets at which the player/patient is encouraged to direct stereo preferred retinal locus 28.

According to example embodiments of the invention, it is necessary for the player/patient to utilize binocular vision in order to successfully play the game. If the player/patient utilizes only one eye independently the player/patient will see either right eye images 36 alone or left eye images 38 alone. Under monocular circumstances it is not possible for the player/patient to align shooting station 44 with attacking aliens 46 in order to successfully eliminate attacking aliens 46 and successfully play the game. Thus, playing the game encourages or forces the player/patient to utilize their remaining vision in a binocular fashion and facilitates establishment of a new stereo PRL 28. Establishment of a new stereo PRL 28 leads to improved binocularity and stereopsis.

Figure 4:
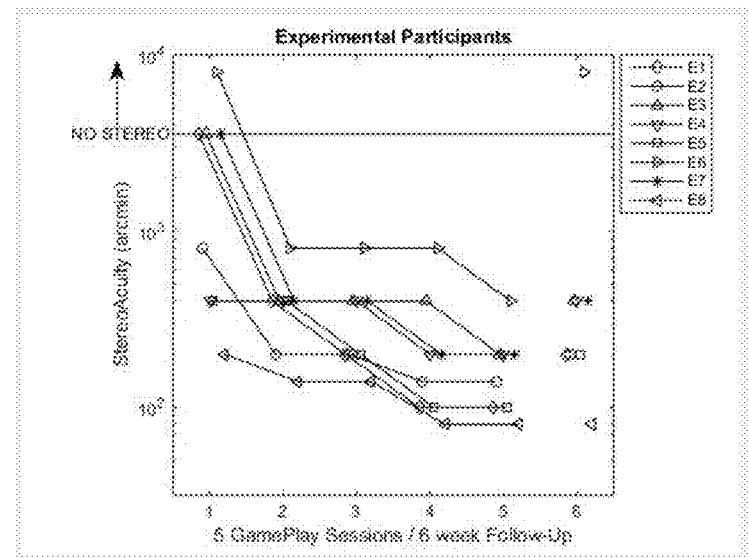
FIG. 4 depicts a graph demonstrating changes in stereo acuity over the course of five game playing sessions for eight experimental participants.
Figure 5:
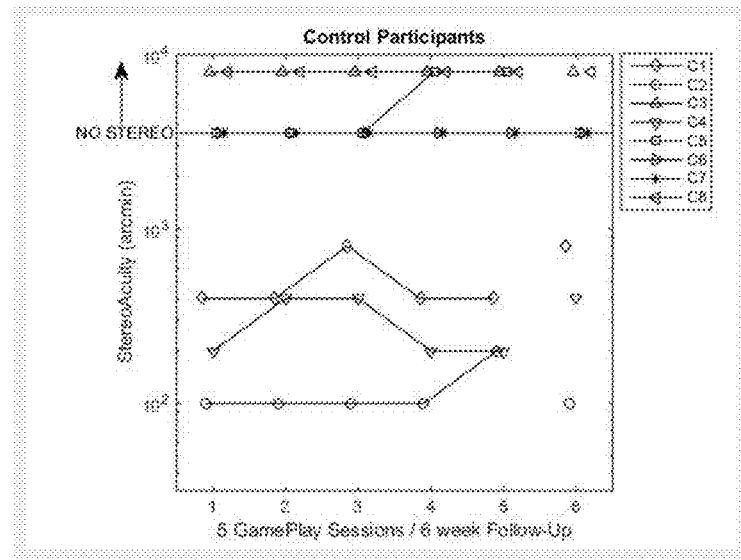
FIG. 5 depicts a graph demonstrating changes in stereo acuity over the course of five game playing sessions for eight control participants.
Figure 6:
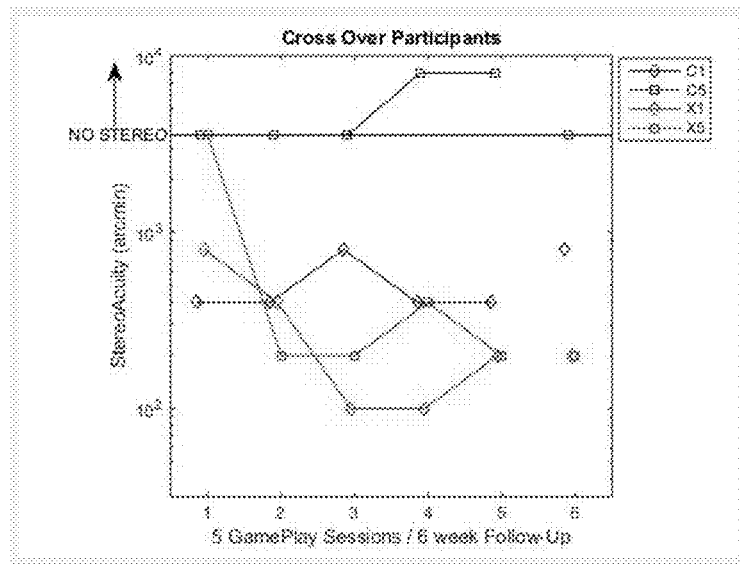
FIG. 6 depicts a graph demonstrating changes in stereo acuity over the course of five game playing sessions for crossover participants.

Referring to FIG. 4, both the experimental group and the control group were tested for stereo acuity with Titmus stereo acuity placards. Testing was performed before and after each of five two-hour training sessions. As can be seen in the graphs of FIG. 4-6, the eight participants of the experimental group with central field loss due to age-related macular degeneration demonstrated significant improvements in stereo acuity as measured while eight participants of the control group who played the game without a dichoptic display did not show any significant improvement in stereo acuity. Two individuals from the control group were crossed over to the experimental group and both achieved improvements in stereo vision as well. Anecdotal reports from individuals achieving improvements in stereo acuity also suggested improvements in activities of daily living when driving, reading and picking up objects as a result of improved stereo acuity.

Example embodiments of the invention include visual training videogame, including:
  a background screen element visible to both eyes of a player of the game;
  a first movable element visible to only a first eye of the player, the first movable element being movable under control of the videogame software and not under control of the player;
  a second movable element movable under control of the videogame player and visible only to the second eye of the player.

Referring to FIG. 4, stereo acuity results are presented as related to eight experimental participants over five gameplay sessions with six-week follow-up.

Referring to FIG. 5, stereo acuity results are presented as related to eight control group participants over five gameplay sessions with six-week follow-up.

Referring to FIG. 6, stereo acuity results are presented as related to crossover participants participants over five gameplay sessions with six-week follow-up.

Another example embodiment of the invention includes method of improving stereopsis, including:

identifying a patient who has reduced stereo acuity due to a central vision loss in at least one eye, the patient thereby having at least one first area of reduced visual function within their binocular visual field and at least one second area of less-reduced visual function within the binocular visual field;

presenting the patient with animated dichoptic images in which first parts of the animated dichoptic image are seen with a right eye, second parts of the animated dichoptic image are seen with a left eye and third parts of the animated dichoptic image are seen with both eyes; providing the patient with control either of the first parts of the animated dichoptic image or the second parts of the animated dichoptic image while the other of the first parts of the animated dichoptic image or the second parts of the animated dichoptic image is controlled by a computer program;

having the patient interact with the animated dichoptic image by controlling the either of the first parts of the animated dichoptic image or the second parts of the animated dichoptic image to engage with the other of the first parts of the animated dichoptic image or the second parts of the animated dichoptic image thereby facilitating the development of a stereo preferred retinal locus corresponding to an area of a retina that is not within the area of reduced visual function within the binocular visual field.

According to another example embodiment the method further includes performing stereo acuity testing to determine a pre-treatment level of stereo acuity as well as to identify and track changes or improvements that occur during training.

According to another example embodiment, the invention includes a method of improving stereopsis in a patient, including facilitating development of a new stereo preferred retinal locus by presenting the patient with dichoptic images that require simultaneous use of both eyes to accomplish a visual task.

According to another example embodiment, the invention includes performing diagnostic testing selected from a group consisting of ophthalmoscopy, visual field testing, fundus photography, optical coherence tomography, amsler grid. Fluoroscein angiography, indocyanine green angiography and a combination of the foregoing. Such testing is done to identify patients will benefit from the treatment techniques disclosed herein.

According to another example embodiment, the invention includes presenting the dichoptic images by techniques selected from a group consisting of an anaglyph presentation, polarized presentation, alternating shutter presentation, a telebinocular presentation, virtual-reality presentation and a combination of the foregoing.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of improving stereopsis, comprising:

identifying a patient who has reduced stereo acuity due to a central vision loss in at least one eye, the patient thereby having at least one first area of reduced visual function within their binocular visual field and at least one second area of less-reduced visual function within the binocular visual field;

presenting the patient with animated dichoptic images in which at least one first part of the animated dichoptic image is visible to a right eye, at least one second part of the animated dichoptic image is visible to a left eye and at least one third part of the animated dichoptic image is visible to both eyes;

providing the patient with control of the at least one first part of the animated dichoptic image while the at least one second part of the animated dichoptic image is controlled by a computer program wherein the control by the patient of the at least one first part of the animated dichoptic image includes control of animated motions and animated actions of the at least one first part of the animated dichoptic image and wherein the control by the computer of the at least one second part of the animated dichoptic image is independent of the control by the patient and includes control of animated motions and animated actions of the at least one second part of the animated dichoptic image;

having the patient interact with the animated dichoptic image by controlling the at least one first part of the animated dichoptic image of the animated motions and the animated actions of the at least one first part of the animated dichoptic image to engage with the at least one second part of the animated dichoptic image thereby facilitating development of a stereo preferred retinal locus.

2. The method as claimed in claim 1, further comprising encouraging the development of the stereo preferred retinal locus at a location corresponding to an area of a retina that is not within the area of reduced visual function within the binocular visual field.

3. The method as claimed in claim 1, further comprising performing stereo acuity testing to determine a pre-treatment level of stereo acuity.

4. The method as claimed in claim 1, further comprising performing stereo acuity testing to determine a post-treatment level of stereo acuity.

5. The method as claimed in claim 1, further comprising identifying the patient having reduced stereo acuity who has the central vision loss in both eyes wherein an area of central vision loss in the first eye varies in size, shape, severity or a combination of the foregoing as compared to the area of central vision loss in the second eye and wherein the area of central vision loss first eye at least partially overlaps the area of central vision loss in the second eye.

6. The method as claimed in claim 1, further wherein the control by the computer of the at least one second part of the animated dichoptic image includes control of visual characteristics of the at least one second part of the animated dichoptic image.

* * * * *